United States Patent
Bonyak et al.

(10) Patent No.: US 10,383,543 B2
(45) Date of Patent: Aug. 20, 2019

(54) SYMMETRIC SHORT CONTACT FORCE SENSOR WITH FOUR COILS

(71) Applicant: BIOSENSE WEBSTER (ISRAEL) LTD., Yokneam (IL)

(72) Inventors: Yevgeny Bonyak, Haifa (IL); Dror Shlomo Levy, Irvine, CA (US); Doron Moshe Ludwin, Haifa (IL); Eitan Moshe Saba, Haifa (IL); Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 944 days.

(21) Appl. No.: 14/937,998

(22) Filed: Nov. 11, 2015

(65) Prior Publication Data

US 2017/0127974 A1 May 11, 2017

(51) Int. Cl.
*A61B 5/06* (2006.01)
*A61B 18/14* (2006.01)
*A61B 5/0402* (2006.01)
*A61B 18/00* (2006.01)
(Continued)

(52) U.S. Cl.
CPC ............ *A61B 5/062* (2013.01); *A61B 5/0402* (2013.01); *A61B 5/065* (2013.01); *A61B 18/1492* (2013.01); *A61B 2018/00351* (2013.01); *A61B 2018/00357* (2013.01); *A61B 2018/00577* (2013.01); *A61B 2018/00839* (2013.01); *A61B 2034/2051* (2016.02);
(Continued)

(58) Field of Classification Search
CPC ...... A61B 18/1492; A61B 2018/00351; A61B 2018/00357; A61B 2018/00839; A61B 2018/00577
See application file for complete search history.

(56) References Cited

U.S. PATENT DOCUMENTS

| 6,226,542 B1 | 5/2001 | Reisfeld |
| 6,241,724 B1 | 6/2001 | Fleischman et al. |
| 6,301,496 B1 | 10/2001 | Reisfeld |
| (Continued) | | |

FOREIGN PATENT DOCUMENTS

| EP | 2 338 428 A1 | 6/2011 |
| EP | 2 749 240 A2 | 7/2014 |

OTHER PUBLICATIONS

European Search Report dated Mar. 15, 2017 from corresponding European Patent Application No. 16198077.6.

*Primary Examiner* — Xuan M Thai
*Assistant Examiner* — Malina D. Blaise
(74) *Attorney, Agent, or Firm* — Vincent J. Serrao

(57) ABSTRACT

In a flexible catheterization probe a resilient member couples the tip to the distal portion of the probe and is configured to deform in response to pressure exerted on the tip when engaging tissue. A position sensor in the distal portion of the probe senses the position of the tip relative to the distal portion of the probe. The relative position changes in response to deformation of the resilient member. The position sensor generates a signal indicative of the position of the tip responsively to a magnetic field produced by a magnetic field generator located in the position sensor. The position sensor has a first coil of conductive wire having first windings, and three second coils of conductive wire having respective second windings. The second coils are symmetrically distributed about the longitudinal axis of the first coil.

9 Claims, 5 Drawing Sheets

(51) Int. Cl.
    *A61B 90/00*          (2016.01)
    *A61B 34/20*          (2016.01)
(52) U.S. Cl.
    CPC . *A61B 2090/065* (2016.02); *A61B 2562/0223* (2013.01); *A61B 2562/0257* (2013.01)

(56) References Cited

U.S. PATENT DOCUMENTS

| | | |
|---|---|---|
| 6,695,808 B2 | 2/2004 | Tom |
| 6,814,733 B2 | 11/2004 | Schwartz et al. |
| 6,892,091 B1 | 5/2005 | Ben-Haim et al. |
| 6,915,149 B2 | 7/2005 | Ben-Haim |
| 6,997,924 B2 | 2/2006 | Schwartz et al. |
| 7,156,816 B2 | 1/2007 | Schwartz et al. |
| 7,536,218 B2 | 5/2009 | Govari et al. |
| 7,756,576 B2 | 7/2010 | Levin |
| 8,192,354 B2* | 6/2012 | Miyake ............... A61B 90/36 600/117 |
| 8,357,152 B2 | 1/2013 | Govari et al. |
| 9,459,124 B2* | 10/2016 | Khalfin ............... G01D 18/00 |
| 10,131,033 B2* | 11/2018 | Maloney ............. B24B 27/0038 |
| 2001/0047133 A1* | 11/2001 | Gilboa .................. A61B 5/06 600/429 |
| 2004/0068178 A1* | 4/2004 | Govari ................. A61B 90/10 600/424 |
| 2006/0278072 A1* | 12/2006 | Kent .................. A61M 25/0021 95/43 |
| 2007/0100332 A1 | 5/2007 | Paul et al. |
| 2008/0275465 A1 | 11/2008 | Paul et al. |
| 2008/0288038 A1 | 11/2008 | Paul et al. |
| 2009/0093806 A1 | 4/2009 | Govari et al. |
| 2009/0138007 A1* | 5/2009 | Govari ................ A61B 1/0008 606/33 |
| 2010/0063478 A1 | 3/2010 | Selkee |
| 2010/0148286 A1 | 6/2010 | Kim et al. |
| 2011/0152856 A1* | 6/2011 | Govari .............. A61B 18/1492 606/34 |
| 2011/0153252 A1* | 6/2011 | Govari ................ A61B 5/1495 702/98 |
| 2011/0290037 A1 | 12/2011 | Delapierre et al. |
| 2012/0197109 A1* | 8/2012 | Hartmann ............. A61B 34/20 600/424 |
| 2012/0259194 A1 | 10/2012 | Selkee |
| 2012/0283552 A1 | 11/2012 | Hall et al. |
| 2013/0296692 A1 | 11/2013 | Vanney et al. |
| 2014/0024969 A1* | 1/2014 | Govari ................ A61B 1/0008 600/587 |
| 2014/0187917 A1* | 7/2014 | Clark .................... A61B 5/062 600/424 |
| 2016/0228180 A1* | 8/2016 | Sliwa .................. A61B 5/6885 |
| 2018/0228557 A1* | 8/2018 | Darisse .............. A61B 1/00149 |
| 2018/0256110 A1* | 9/2018 | Govari .................. A61B 5/107 |
| 2018/0256247 A1* | 9/2018 | Govari .................. A61B 34/20 |

* cited by examiner

SYMMETRIC SHORT CONTACT FORCE SENSOR WITH FOUR COILS

BACKGROUND OF THE INVENTION

1. Field of the Invention.

This invention relates to medical devices. More particularly, this invention relates to a medical device for measuring force applied to parts of the body.

2. Description of the Related Art.

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Verification of physical electrode contact with the target tissue is important for controlling the delivery of ablation energy. Attempts in the art to verify electrode contact with the tissue have been extensive, and various techniques have been suggested. For example, U.S. Pat. No. 6,695,808 describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. U.S. Pat. No. 6,241,724 describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey RF energy to these elements, and not to other elements that are in contact only with blood.

A further example is presented in U.S. Pat. No. 6,915,149. This patent describes a method for mapping a heart using a catheter having a tip electrode for measuring local electrical activity. In order to avoid artifacts that may arise from poor tip contact with the tissue, the contact pressure between the tip and the tissue is measured using a pressure sensor to ensure stable contact.

U.S. Patent Application Publication 2007/0100332 describes systems and methods for assessing electrode-tissue contact for tissue ablation. An electromechanical sensor within the catheter shaft generates electrical signals corresponding to the amount of movement of the electrode within a distal portion of the catheter shaft. An output device receives the electrical signals for assessing a level of contact between the electrode and a tissue.

Impedance-based methods for assessing catheter-tissue contact that are known in the art typically rely on measurement of the magnitude of the impedance between an electrode on the catheter and a body-surface electrode. When the magnitude is below some threshold, the electrode is considered to be in contact with the tissue. This sort of binary contact indication may be unreliable, however, and is sensitive to changes in the impedance between the body-surface electrode and the skin.

U.S. Patent Application Publication Nos. 2008/0288038 and 2008/0275465, both by Sauarav et al., which are herein incorporated by reference, describe an electrode catheter system, which may comprise an electrode adapted to apply electric energy. A measurement circuit adapted to measure impedance may be implemented between the electrode and ground as the electrode approaches a target tissue. A processor or processing units may be implemented to determine a contact condition for the target tissue based at least in part on reactance of the impedance measured by the measurement circuit. In another embodiment, the contact condition may be based on the phase angle of the impedance.

SUMMARY OF THE INVENTION

According to disclosed embodiments of the invention, a contact force sensor for a catheter has enhanced immunity to metal interference. In one embodiment a cylindrical receiving coil is centrally disposed in a nitinol housing and is operative for estimation of force value. Three elliptic coils are assembled about the cylindrical receiving coil, with 120 degrees between them. The elliptic coils are used for estimation of force value and direction. Because the receiving coil is installed centrally, deep within the center of the sensor, and remote from the nitinol housing, metal objects located less than about 1 mm to the sensor, such as the catheter shaft, do not cause a significant force measurement error. Moreover, the effects of metallic objects are unaffected by the orientation of the catheter tip due to the symmetrical design of the contact force sensor.

There is provided according to embodiments of the invention a flexible probe whose distal portion is adapted for insertion into a body cavity of a patient. The distal tip of the probe is configured to be brought into contact with tissue in the body cavity. A resilient member couples the distal tip to the distal portion of the probe and is configured to deform in response to pressure exerted on the distal tip when the distal tip engages the tissue. A position sensor is disposed in the distal portion of the probe for sensing a position of the distal tip relative to the distal portion of the probe, which changes in response to deformation of the resilient member. The position sensor is configured to generate a signal indicative of the position of the distal tip responsively to a magnetic field. A magnetic field generator is provided within the distal tip for generating the magnetic field, wherein the position sensor includes a first coil of conductive wire having first windings, and three second coils of conductive wire having respective second windings. The second coils are symmetrically distributed about the longitudinal axis of the first coil.

According to still another aspect of the apparatus there are exactly three second coils.

According to yet another aspect of the apparatus, the first windings are directed about the longitudinal axis of the first coil.

According to still another aspect of the apparatus, the second coils are elliptical coils.

According to an additional aspect of the apparatus, the second coils are in contact with the first coil.

According to one aspect of the apparatus, the major axes of the elliptical coils are parallel to the longitudinal axis of the first coil.

According to another aspect of the apparatus, the second windings are directed from the first vertex to the second vertex of the elliptical coils, respectively.

According to a further aspect of the apparatus, the first coil is wound about a hollow tube.

According to yet another aspect of the apparatus, the second coils are air core inductors.

There is further provided according to embodiments of the invention a method, which is carried out by inserting the distal portion of a flexible probe into a body cavity of a patient, bringing the distal tip of the probe into contact with tissue in the body cavity, coupling the distal tip to the distal portion of the probe with a resilient member that is configured to deform in response to pressure exerted on the distal tip when the distal tip engages the tissue, and sensing a position of the distal tip relative to the distal portion of the probe with a position sensor disposed in the distal portion of the probe. The position of the distal tip changes in response to deformation of the resilient member. The method is further carried out by generating a signal indicative of the position of the distal tip responsively to a magnetic field that is generated in a vicinity of the distal tip, providing a magnetic field generator within the distal tip for generating the magnetic field. The position sensor includes a first coil of conductive wire and three second coils of conductive wire. The second coils are symmetrically distributed about the longitudinal axis of the first coil.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

System Overview.

Figure 1:
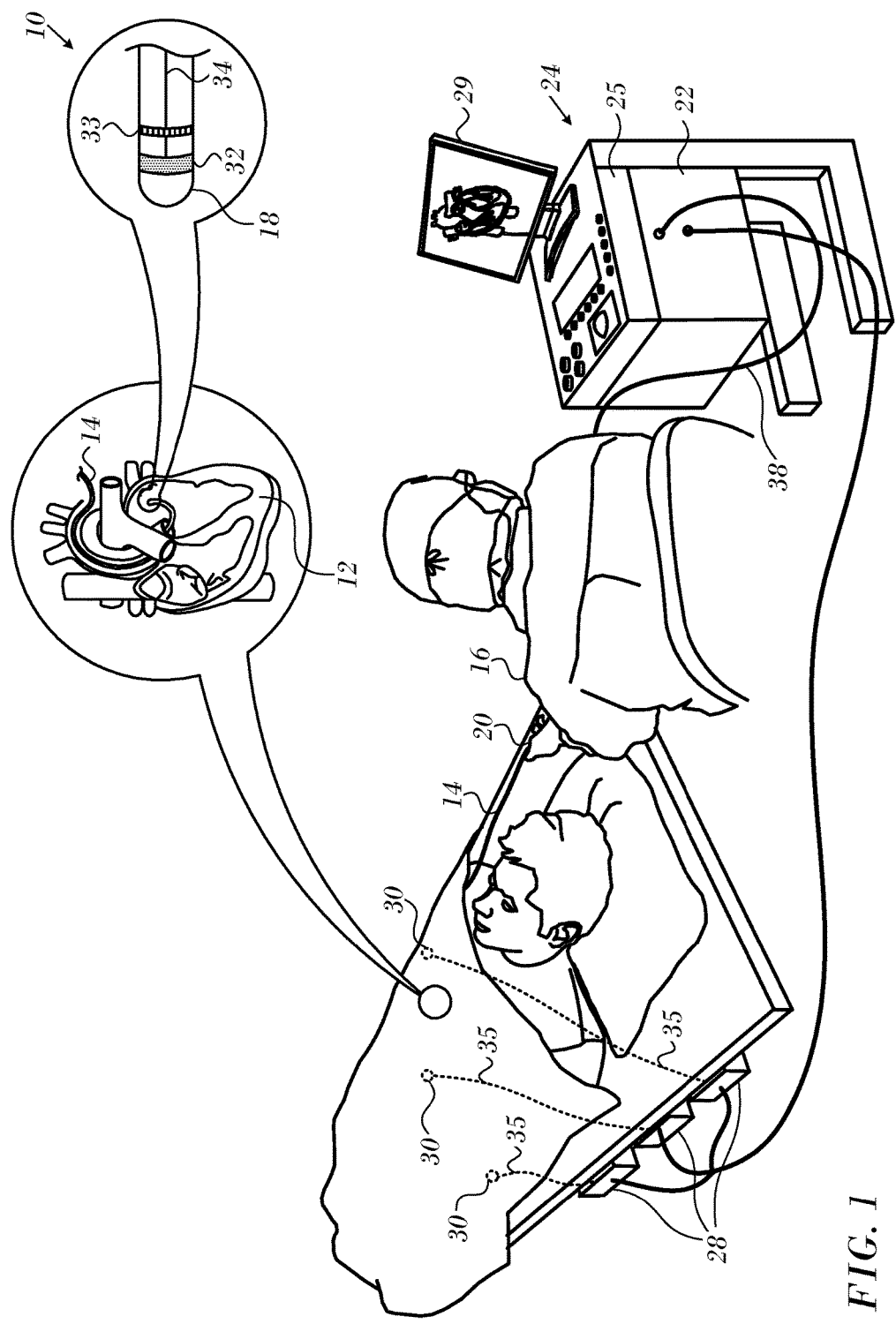
FIG. 1 is a pictorial illustration of a system for performing catheterization procedures on a heart, in accordance with a disclosed embodiment of the invention.

Turning now to the drawings, reference is initially made to FIG. 1, which is a pictorial illustration of a system 10 for evaluating electrical activity and performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 60° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultra-sound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

In order to generate electroanatomic maps, the processor 22 typically comprises an electroanatomic map generator, an image registration program, an image or data analysis program and a graphical user interface configured to present graphical information on the monitor 29.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images.

Contact Force Sensor.

Figure 2:
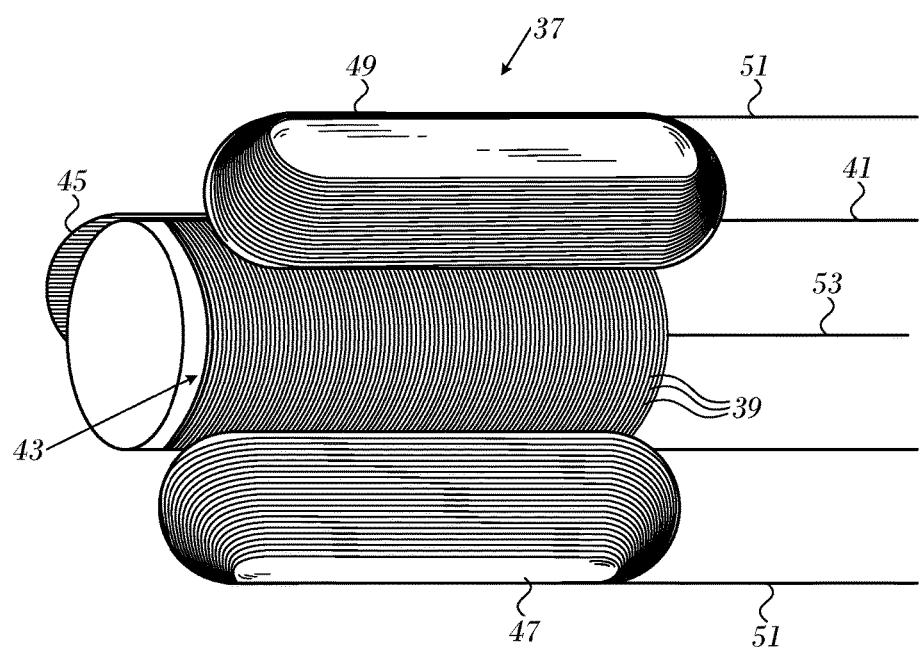
FIG. 2 is a schematic oblique elevation of a contact force sensor 37 in accordance with an embodiment of the invention.

Reference is now made to FIG. 2, which is a schematic oblique elevation of a contact force sensor 37 in accordance with an embodiment of the invention. A central coil 39 comprises one or two layers of 10 µ enameled copper wire are wound about a cylindrical air-filled polyimide tube 41 to form a central air core inductor 43. The diameter of the tube 41 is typically about 0.8-0.9 mm. Typical dimensions for one layer of 10 µm wire wound about the polyimide tubing are: outer diameter 0.947 mm, length 2.15 mm, and 350 turns. The central coil 39 is wound generally transverse to the longitudinal axis of the tube 41.

Surrounding the inductor 43 are a plurality of elliptical coils. Three elliptical coils 45, 47, 49 are shown in FIG. 2.

Each comprises more than 10 layers of 10 µ enameled copper wire to create an air core elliptic coil having major and minor axes, which are typically 2.15-2.35 and 0.6-0.8 cm, respectively. In this embodiment elliptical coils 45, 47, 49 are disposed about the central coil 39 with the major axis of each ellipse being parallel to the longitudinal axis of the central coil 39. The windings of the elliptical coils 45, 47, 49 are each generally directed from one vertex to the other vertex of the respective ellipses. The elliptical coils 45, 47, 49 are symmetrically distributed about the longitudinal axis of the tube 41. Leads 51 conduct signals from the elliptical coils 45, 47, 49 to a processor (not shown). A lead 53 conducts signals from the central coil 39 to the processor.

Figure 3:
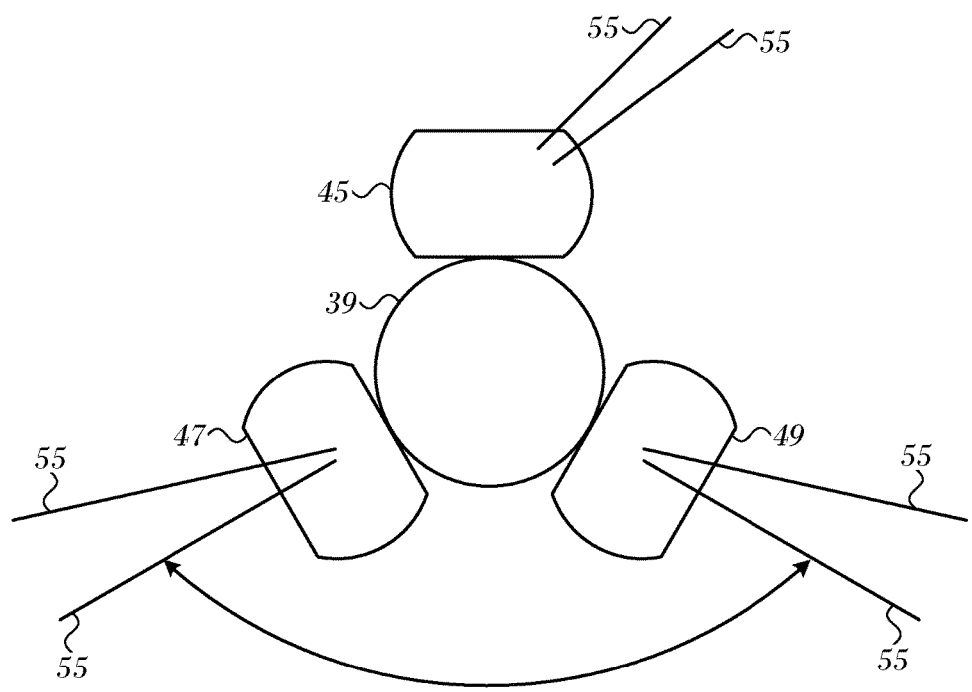
FIG. 3 is a sectional view through a sensor in accordance with an embodiment of the invention.

Reference is now made to FIG. 3, which is a sectional view through a sensor in accordance with an embodiment of the invention. Distribution of the elliptical coils 45, 47, 49 at 120° intervals is demonstrated on this view. There is a contacting relationship between each of the forms of the elliptical coils 45, 47, 49 and the central coil 39. Wire leads 55 are provided for conducting signals from the coils.

Figure 4:
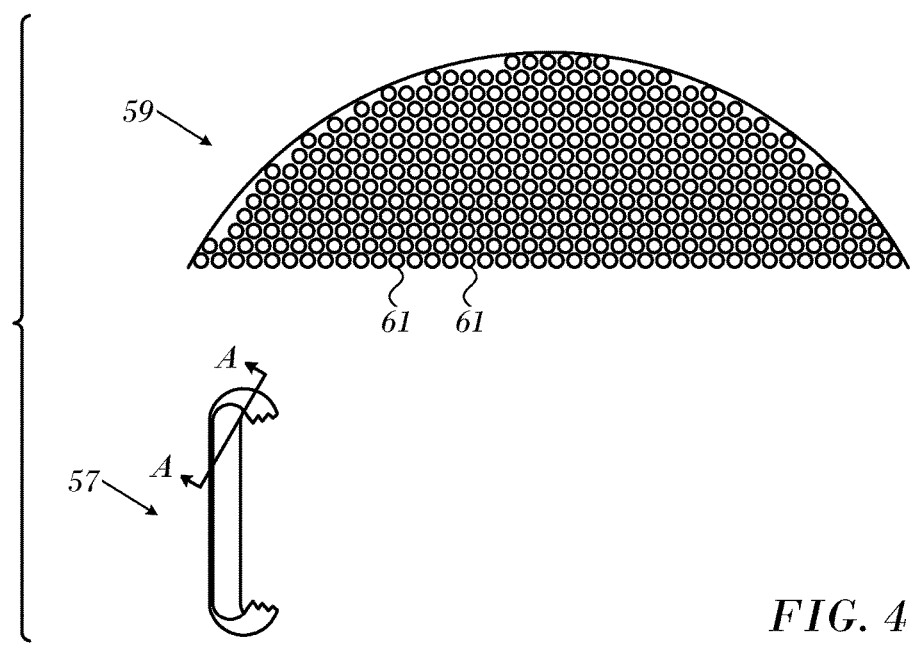
FIG. 4 is a schematic partial sectional view through an air core elliptical coil in accordance with an embodiment of the invention.

Reference is now made to FIG. 4, which is a schematic partial view through an air core elliptic coil 57, in accordance with an embodiment of the invention. As shown in a cross section 59 taken through line A-A of coil 57, more than ten layers of wire 61 are wound in an elliptical pattern to form the elliptical air coil.

Figure 5:
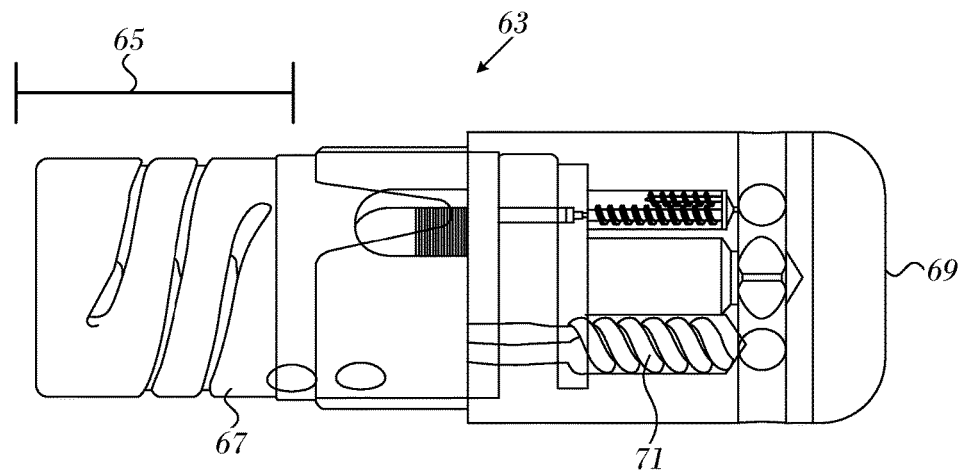
FIG. 5 is an elevation of a distal portion of a cardiac catheter in accordance with an embodiment of the invention.

Reference is now made to FIG. 5, which is an elevation of the distal portion of a cardiac catheter 63, in accordance with an embodiment of the invention. A contact force sensor constructed in accordance with an embodiment of the invention is disposed in a segment 65 of the catheter. Except for the contact force sensor, the catheter 63 may be the catheter described in commonly assigned U.S. Patent Application Publication No. 2009/0093806 by Govari et al., which is herein incorporated by reference. The catheter 63 is a flexible insertion tube, having a distal end 67 for insertion into a body cavity of a patient, and a distal tip 69, which is configured to be brought into contact with tissue in a body cavity. A resilient member 71 couples the distal tip 69 to the distal end 67 and deforms in response to pressure exerted on the distal tip 69. When the distal tip 69 engages the tissue. The contact force sensor within the probe senses a position of the distal tip 69 relative to the distal end 67 of the catheter 63, The position and the sensor readings change in response to deformation of the resilient member 71.

Figure 6:
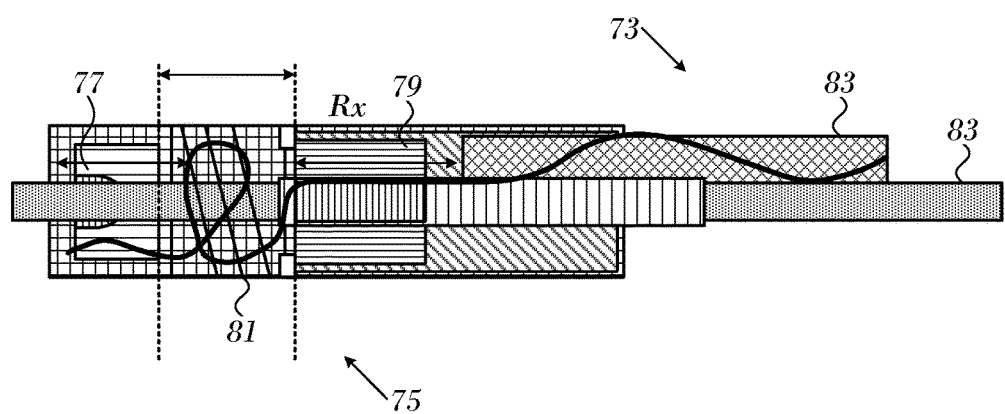
FIG. 6 is a schematic sectional view through the distal portion of a cardiac catheter including a contact force sensor that is constructed and operative in accordance with an embodiment of the invention.

Reference is now made to FIG. 6, which is a schematic longitudinal sectional view through the distal portion of a cardiac catheter 73, which has been modified by replacement of a conventional contact force sensor by a contact force sensor 75 that is constructed and operative in accordance with an embodiment of the invention. From the perspective of the operator, the operation of the catheter 63 does not differ from an unmodified version. However, there is one less coil and one less electrical channel than in the unmodified version. A transmitting coil 77 is provided as a signal source for the central coil and the elliptical coils in the contact force sensor 75. Four receiving coils 79, (best seen in FIG. 2 as the elliptical coils 45, 47, 49 and central coil 39) are present. The contact force sensor 75 receives signals from external field generating coils 28 (FIG. 1) and the transmitting coil 77, so that the four receiving coils 79 are exposed to four electromagnetic fields at respective frequencies. Other components of the contact force sensor 75 include a spring 81 disposed between the transmitting coil 77 and the receiving coils 79. Various typically asymmetric metallic structures 83 having functions that are beyond the scope of this disclosure may be present in the cardiac catheter 73. As noted above, the metallic structures 83 can adversely affect readings of the contact force sensor 75.

Operation.

As noted above, the elliptical coils 45, 47, 49 provide information on force value and direction. The central coil 39 provides information on the force value. Reverting to FIG. 2, the signals received in the elliptical coils 45, 47, 49 and the central coil 39 are measured and the ratio between the transmitted signal produced by transmitting coil 77 (FIG. 6) and the received signal from the elliptical coils is calculated for each of the elliptical coils 45, 47, 49 and the central coil 39 using signals from the field generating coils 28 (FIG. 1) at respective frequencies:

$$S_i = \left| \frac{RX_{force_i}}{TX} \right|_{i=1,2,3}$$

The ratio between the transmitted and received signal is normalized with a measurement taken when no force is applied to the tip of the catheter.

$$Sz_i = \left| \frac{S_i}{S_{zero_i}} - 1 \right|_{i=1,2,3}$$

After calibration, the force applied to the tip of the catheter is estimated as follows:

$$\vec{F}\text{estimated vector} = \begin{bmatrix} M_{11} & M_{12} & M_{13} \\ M_{21} & M_{22} & M_{23} \\ M_{31} & M_{32} & M_{33} \end{bmatrix} \cdot \begin{bmatrix} Sz_1 \\ Sz_2 \\ Sz_3 \end{bmatrix} = \begin{bmatrix} F_x \\ F_y \\ F_z \end{bmatrix} \quad \text{Eq. (1)}$$

$$F = \sqrt{F_x^2 + F_y^2 + F_z^2}, \; \phi = \tan^{-1}\left(\frac{\sqrt{F_x^2 + F_y^2}}{F_z}\right), \; \varphi = \tan^{-1}\left(\frac{F_x}{F_y}\right),$$

where $M_{ij}$ are calibration elements calculated for a given matrix of N force measurements, each comprising components $F_x$, $F_y$, $F_z$. Four force measurements can be obtained from the three elliptical coils 45, 47, 49 and the central coil 39.

Signals from all four coils provide a solution for magnitude and direction.

For all four coils the force vector is:

$$\vec{F} = \begin{bmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{bmatrix} \cdot \begin{bmatrix} Sz_1 \\ Sz_2 \\ Sz_3 \\ Sz_4 \end{bmatrix} = \begin{bmatrix} F_x \\ F_y \\ F_z \\ F_w \end{bmatrix} \quad \text{Eq. (2)}$$

When only a single coil is being used, the equation reduces to.

$$\vec{F} = [M1] * [Sz1] = [Fx] \quad \text{Eq. (3)}$$

Signals from three elliptical coils provide a less precise solution for magnitude and direction than from all four coils.

Signals taken only from the central coil provide a solution for magnitude, but not direction.

The magnitude of readings from the contact force sensor are dependent on the hardware configuration of the catheter and the electronics. Typically, the maximum axial force detected is 150 gm. A lateral force can be accurately measured up to 30 gm, above which accuracy suffers. The resolution of the force measurement is less than 1 gm.

Figure 7:
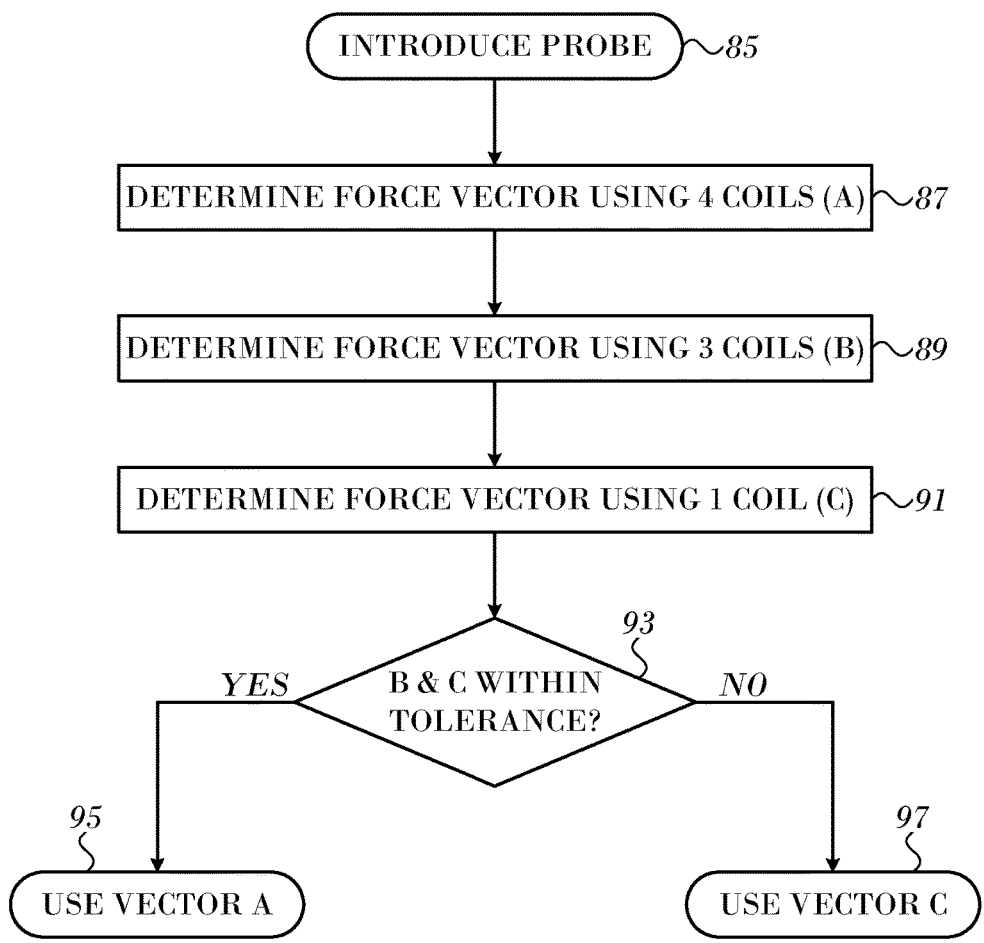
FIG. 7 is a flow chart of a method of determining contact between a probe and a tissue in accordance with an embodiment of the invention.

Reference is now made to FIG. 7, which is a flow chart of a method of determining contact between a probe and a tissue in accordance with an embodiment of the invention. The process steps are shown in a particular linear sequence for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 85 a probe is introduced conventionally into the body of a subject and brought into contact with a tissue. Metallic objects are assumed to be present in sufficient proximity to affect the readings of the contact force sensor.

Next, at step 87 a force vector (A) is determined using all four coils of the sensor, e.g., elliptical coils 45, 47, 49 and central coil 39 (FIG. 2) according to Equation 2, Next, at step 89 a force vector (B) is determined using the three elliptical coils 45, 47, 49 according to Equation 1.

Next, at step 91 a force vector (C) is determined using only the central coil 39 according to Equation 3

Next, at decision step 93, it is determined if the force magnitude (C) obtained from the central coil 39 in step 91 is in agreement with the force magnitude (B) obtained from the elliptical coils 45, 47, 49 in step 89 according to a predetermined criterion, e.g., the two force magnitudes differ by less than 5%. This criterion may be varied in different applications.

If the determination at decision step 93 is affirmative, then control proceeds to final step 95. The force magnitude and directional readings from all four coils (A) that was obtained in step 87 are used to evaluate contact between the probe and the tissue.

If the determination at decision step 93 is negative, then at final step 97 the force magnitude information obtained from the central coil 39 (C) is used to evaluate contact between the probe and the tissue. Directional information is not available.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
    inserting a flexible probe into a body cavity of a patient, the flexible probe having a distal portion and a distal tip coupled to the distal portion by a resilient member, the resilient member being configured to deform in response to pressure exerted on the distal tip when the distal tip engages tissue within the body cavity, a magnetic field generator located within the distal tip for generating a magnetic field and a position sensor disposed in the distal portion, the position sensor comprising a first coil of conductive wire having a longitudinal axis and first windings and three second coils of conductive wire having respective second windings, the second coils being symmetrically distributed about the longitudinal axis of the first coil;

bringing the distal tip of the probe into contact with the tissue in the body cavity;

sensing a position of the distal tip relative to the distal portion of the probe with the position sensor, wherein the position of the distal tip changes in response to deformation of the resilient member, generating a signal indicative of the position of the distal tip responsively to a magnetic field that is generated in a vicinity of the distal tip, wherein generating the signal comprises determining a first force vector using signals from the first coil and the three second coils;

determining a second force vector using signals only from the three second coils;

determining a third force vector using signals only from the first coil;

when the second force vector and the third force vector differ by less than a threshold using the first force vector as the signal indicative of the position of the distal tip; and when the second force vector and the third force vector differ by more than the threshold using the third force vector as the signal indicative of the position of the distal tip.

2. The method according to claim 1, in which there are exactly three second coils.

3. The method according to claim 1, wherein the first windings are directed about the longitudinal axis of the first coil.

4. The method according to claim 1, wherein the second coils are elliptical coils having major axes, a first vertex and a second vertex, respectively.

5. The method according to claim 4, wherein the second coils are in contact with the first coil.

6. The method according to claim 4, wherein the major axes of the elliptical coils are parallel to the longitudinal axis of the first coil.

7. The method according to claim 4, wherein the second windings are directed from the first vertex to the second vertex, respectively.

8. The method according to claim 1, wherein the first coil is wound about a hollow tube.

9. The method according to claim 1, wherein the second coils are air core inductors.

* * * * *